United States Patent [19]

Babb

[11] 4,316,466

[45] Feb. 23, 1982

[54] BODY FLUID DRAINAGE DEVICE

[75] Inventor: Albert L. Babb, Seattle, Wash.

[73] Assignee: Biomedics, Inc., Arlington Heights, Ill.

[21] Appl. No.: 163,888

[22] Filed: Jun. 27, 1980

[51] Int. Cl.³ .............................................. A61M 1/00
[52] U.S. Cl. ..................................... 128/278; 128/635
[58] Field of Search ........... 128/213 A, 213 R, 214 R, 128/278, 632, 633, 637, 635, 1 R, 214 F

[56] References Cited

U.S. PATENT DOCUMENTS

| 3,655,123 | 4/1972 | Judson et al. | 128/214 R |
|---|---|---|---|
| 3,838,682 | 10/1974 | Clark et al. | 128/635 |
| 4,006,743 | 2/1977 | Kowarski | 128/214 R |
| 4,258,717 | 3/1981 | Bisera et al. | 128/637 |

Primary Examiner—Robert W. Michell
Assistant Examiner—T. J. Wallen

[57] ABSTRACT

An apparatus is provided suitable for use in draining liquid from inside the human body. The apparatus incorporates two reciprocating pumps and a pair of inlet and outlet valves driven by a common linkage system. One pump draws fluid from a reservoir of additive fluid and mixes the additive with the fluid drawn from the body by the second pump. The mixture is discharged to a common collection means. A pressure sensor terminates the pumping if the fluid pressure in the flow path joining the apparatus with the body becomes abnormal. The apparatus may be mounted externally on the body of the patient and may be driven by a portable source of power. Major components may be changed quickly and easily if the flow capacity is to be changed or if a component must be replaced.

25 Claims, 4 Drawing Figures

BODY FLUID DRAINAGE DEVICE

TECHNICAL FIELD

This invention relates generally to an apparatus for withdrawing fluid from the human body, and, in particular, it relates to a device that simultaneously withdraws fluid from the human body and mixes with that fluid a liquid additive containing one or more compounds or agents in a pre-selected proportion before discharging the mixture to a collection point.

BACKGROUND OF THE INVENTION

Clinical studies and tests have shown that thoracic duct drainage is a mode of therapy by which the deleterious effects of the cell-mediated immune response in man could be abrogated by removal of thoracic duct lymphoytes[1]. Thoracic duct drainage is a technique by which the thoracic duct lymph and its contained lymphocytes are diverted from the body to eliminate one or all of the lymph components. The presumed mechanism is depletion of lymphocytes and possibly depletion of certain immune globulins. In order to produce attenuation, experience has demonstrated that drainage must be continuous for periods of one month or longer.
[1] H. K. Johnson et al., Transplantation Proceedings, Volume IX, No. 3 (September), 1977).

Presently the procedure is costly and technically demanding because the lymph must be processed to remove the cells and then re-infused intravenously. Alternatively, the lymph is discarded and replaced by human serum albumin. Cost estimates for a month of treatment are in the order of twenty to fifty thousand dollars. Although donor or cadaver kidney transplantation becomes more expensive with thoracic duct drainage, there is little or no added morbidity or mortality, and improved graft survival rates are generated. If the cost could be reduced and the technique simplified, greatly improved donor and cadaveric transplant results would be assured.

In general the flow rates and the quantity of bodily fluid involved is somewhat variable. One investigator[2] reported on the concept of extra-corporeal lymph dialysis and envisioned flow rates ranging from 1.5 to 2.5 liters per day. However, in four patients the flow rate ranged from 4 to 14 liters per day and averaged in excess of six liters per day. Since no means of bypass was available, it was necessary to collect, dialyze, and infuse the total flow from each patient daily.
[2] Serles et al., Transactions of the American Society for Artificial Internal Organs, Volume 11, page 165, 1965.

In addition, fluid pressure must be carefully controlled. Animal studies have shown that clamping the thoracic duct cannula[3] would cause the rapid development of alternate channels which would completely divert all flow from the cannulated duct. Attempts to connect the thoracic duct cannula directly to the venous catheter were only successful when duct pressure exceeded the venous pressure. In fact, since duct pressure varies with metabolic rate, intervals exist when venous pressure substantially exceeds duct pressure. Under these conditions blood could enter the venous catheter and clot.
[3] loc. cit.

It appears, therefore, that a device used to drain fluid from a thoracic duct must be one that does not produce any back-pressure favorable to the development of collateral channels or cause the lymphatic valves[4] to become incompetent. On the other hand, if the suction pressure is too great the thoracic duct could be forced to collapse.
[4] Goss, Gray's Anatomy, Lea & Felshiger, 29th Ed., 1973, page 735

Moreover, since lymph flow rates can vary anywhere from three to one thousand milliliters per hour, the apparatus used to drain or pump the fluid from the duct must adjust almost instantly to this range of flow rates.

In addition, the apparatus should have several channels or flow paths—one for metering proportionately an anticoagulant such as heparin or preferably trisodium citrate in a saline solution and a second flow path for infusing anti-humoral drugs, for example.

The lymph fluid drawn off by the apparatus would be collected, filtered, treated and/or purified and then redirected back into the patient. The removed lymphocytes would be discarded or used for some other purpose. Another method is phoresis or cytophoresis. Another possibility, under investigation, is to install an extra-corporal bed to which the lymphocytes can attach themselves. In addition, a protein A absorbent may be employed to remove the immune complexes in the lymph. Finally, the drainage procedure provides a ready source of antigen for the production of antilymphocyte serum.

Thus, prolonged lymphodepletion by way of thoracic duct drainage can provide excellent pre-transplant immunosuppression for donor or cadaver kidney recipients. A simple, reliable, easy to control device reducing the constant attention and diligence of medical and nursing personnel would improve the acceptance of this technique and reduce present costs.

SUMMARY OF THE INVENTION

In accordance with the present invention an apparatus is provided that simultaneously draws fluid from inside a patient's body and mixes with that fluid a liquid additive producing a fluid mixture of a pre-selected concentration. The apparatus includes unique features to prevent an adverse effect on the patient resulting from withdrawing fluid too quickly or from excess back pressure. Specifically, the apparatus employs a frame to which are attached tubing or piping defining two passageways or flow paths. One flow path is called "the body fluid flow path" since the inlet to that flow path is adapted to be removably joined to a source of fluid within the patient. The second flow path is called the "additive fluid flow path" since the inlet is adapted to be removably joined to the reservoir of an additive fluid such as an anticoagulant, a fluid containing agents such as cytotoxic materials, or other medicaments.

Each flow path contains a reciprocating pumping means, an inlet valve and an outlet valve. The fluid discharged from the additive fluid flow path joins the body fluid flow path at a location upstream of the reciprocating pumping means and downstream of the inlet valve in the body fluid flow path. The confluence of the two flow paths is the place where body fluid and additive fluid are mixed together. The outlet of the body fluid flow path is adapted to be joined to a container suitable for collecting the mixture of additive fluid and body fluid.

A motor means, mounted on the frame, operates the inlet and outlet valves and the reciprocating pumping means in each of the two flow paths. Specifically, the motor means sequences the operation of the inlet and outlet valves and the stroking of the reciprocating pumping means so as to mix the additive fluid with the body fluid and to discharge the mixture to a suitable container.

A fluid pressure sensor means is positioned in the body fluid flow path downstream of the inlet valve and upstream of the associated reciprocating pumping means. The fluid pressure sensor means applies a control signal to the motor means. If the pressure in the body fluid flow path upstream of the associated reciprocating pumping means becomes abnormal, the motor means is shut off. This insures that an adverse reaction is not produced in the patient's body by the operation of the apparatus.

Each inlet and outlet valve preferably consists of a section of flexible tubing that is juxtaposed between a stop joined to the frame and a pinching means which is used to press the walls of the flexible tube against the stop to shut off flow therethrough. A cam and follower operated by the same device powering the reciprocating pumping means may be used to sequence the pinching means. The motor means incorporates features which allow the stroke of the reciprocating pumping means to be adjusted and hence the amount of fluid transferred by the reciprocating pumping means. The inherent versatility, simplicity, and integrated relationship of the components forming the apparatus allows medical personnel to easily understand operation of the components and to quickly troubleshoot them should any difficulty be encountered.

Numerous other advantages and features of the present invention will become readily apparent from the following detailed description of the invention and the embodiments illustrated therein, from the claims, and from the accompanying drawings.

DETAILED DESCRIPTION

Figure 1:
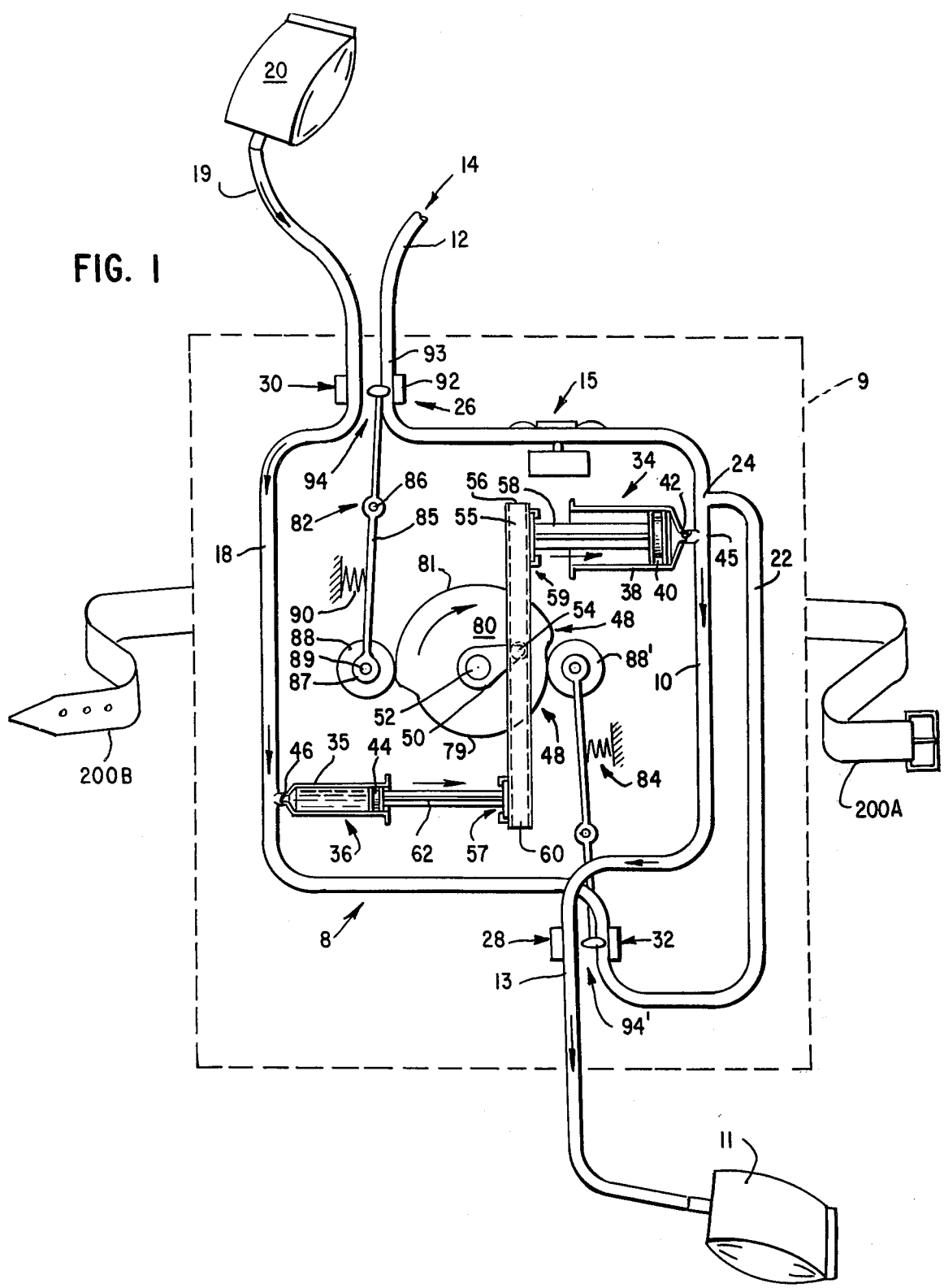
FIG. 1 is a schematic diagram illustrating the major components of the present invention in a first position.

While this invention is susceptible of embodiment in many different forms, there is shown in the drawings and will herein be described in detail several specific embodiments, with the understanding that the present disclosure is to be considered as an exemplification of the principles of the invention and is not intended to limit the invention to the specific embodiments illustrated.

Turning to the drawings, FIG. 1 illustrates the major components 8 of the present invention and one embodiment of the apparatus used to actuate the movable components. For purposes of orientation, the major flow paths will be described first followed by a detailed discussion of the specific components included in those flow paths. The major components 8 are carried on a common frame 9.

Briefly, these components include: piping or tubing forming two major flow paths 10 and 18; pumping means 34 and 36; valving means 26, 28, 30, and 32; fluid pressure sensor means 15; and a motor means 48 which is used to operate the valving means and the pumping means. Together they form a closed, sterile flow network. The piping or tubing forming the two flow paths 10 and 18, and the components in fluid communication with the flow paths are fabricated from materials which are easy to clean and sterilize after use. Preferably, the tubing is joined to the frame 9 and the other components in such a manner that it may be easily removed and discarded after use. For convenience and to simplify fabrication, the two flow paths 10 and 18 can be formed from clear plastic tubing. The other components joined to the tubing, such as the pumping means 34 and 36, may be formed from plastic or glass.

The first flow path or flow stream 10 is used to conduct fluid from the body of a patient represented by numeral 14, to a collection point or removable collection chamber 11 such as a transfer pack or sterile plastic bag. Because of this relationship, the first flow path 10 will be referred to as the "body fluid flow path." The second flow path or flow stream 18 is used to conduct additive fluid from an external supply tank or reservoir 20 to the body fluid flow path 10 where the additive fluid is mixed with the fluid drawn from the body. Alternatively, the second flow path 18 will be referred to as the "additive fluid flow path."

Specifically, one end 12 of the body fluid flow path 10 is adapted to be joined to an interior duct or channel in the body 14 of the patient. The other end 13 of the body fluid flow path 10 is adapted to be joined or removably connected to a collection means or chamber 11. It should be understood that, although the collection means 11 at the outlet of the body fluid flow path 10 is illustrated as a plastic bag (FIG. 1), the outlet may be joined to a filter, or other device used to process the fluid drawn from the patient's body 14. One end 19 of the second flow path 18 is adapted to be removably joined to or connected to an external supply tank or reservoir 20 of additive fluid. The other end 22 of the second flow path 18 is joined to the first flow path 10 at a point 24 intermediate the two ends 12 and 13 of the first flow path 10. This intermediate point 24 forms the "confluence" of the two flow streams 10 and 18. It is here that the additive fluid is mixed with the fluid drawn from the body.

Returning to the first flow path 10, valving means are positioned at either end 12 and 13 of the flow path. Specifically, an inlet valve means 26 is located at that end 12 joined to the duct in the body of the patient 14. An outlet valve means 28 is located at the end 13 of the first flow path 10 that discharges the mixture of body fluid and additive fluid to the collection means 11. Similarly, the second flow path 18 has an inlet valve means 30 at that end 19 joined to the reservoir 20 of additive fluid and an outlet valve means 32 at that end 22 joined to the first flow path 10. The operation and sequencing of these valves will be explained at a later point in this discussion.

Each flow path 10 and 18 includes a reciprocating pumping means to transfer fluid therethrough. A first reciprocating pumping means 34 is located intermediate the two ends 12, 13 of the first flow path 10. Likewise, a second reciprocating pumping means 36 is located in the second flow path 18 at a point intermediate the two ends 19 and 22 of that flow path. Each reciprocating pumping means 34 and 36 is formed from a fluid reservoir and a piston. Specifically, the first reciprocating pumping means 34 includes a cylindrical enclosure or first cylinder 38 having one open end. The open end is plugged by a piston 40 (alternatively referred to as the "first piston" since it fits within the first cylinder 38). The closed end of the cylinder 38 has an opening 42 that is in flow communication with the body fluid flow path 10. This opening 42 defines the "inlet" and the "outlet" of the first reciprocating pumping means 34.

Likewise, the second reciprocating pumping means 36 is formed from a second cylinder 35 having an open end and a closed end. The open end is plugged by a piston 44. The closed end has an opening 46 that is in communication with the second flow path 18. The opening 46 at the end of the second reciprocating pumping means 36 defines the "inlet" and the "outlet" of the second reciprocating pumping means. As the name implies, the pistons 40 and 44 in each of the two cylinders 35 and 38 are driven reciprocally along the longitudinal axis of the enclosures to induce the transfer of fluid. These two pistons 40 and 44 are driven by a motor means 48 which will be explained in detail at a later point in this discussion.

How each reciprocating pumping means 34 and 36 produces pumping action so as to transfer fluid will now be explained. Since each of the two reciprocating pumping means 34 and 36 operates in essentially the same manner, only one will be explained in detail. Turning to the first reciprocating pumping means 34 in the body fluid flow path 10, as the first piston 40 is drawn towards the open end of the cylinder 38 the internal volume of that cylinder in communication with the body fluid flow path 10 increases and fluid fills the first cylinder 38. This is referred to as the "intake" or "suction" portion of the stroke or reciprocating cycle of the first reciprocating pumping means 34.

By examining FIG. 1 it should be appreciated that in order for fluid to be drawn into the first cylinder 38 from the body 14, the inlet valve means 26 has to be open and the outlet valve means 28 has to be shut. Once the piston 40 has been drawn to the end of the first cylinder 38, the suction stroke of the first reciprocating pumping means 34 is completed.

In order for fluid to be forced from the first cylinder 38 into the collection means or chamber 11, the inlet valve means 26 has to be shut and the outlet valve means 28 has to be opened. Once these two valving means 26 and 28 are so positioned, the piston 40 can be forced inwardly towards the closed end of the first cylinder 38. When this is done the fluid contained within the first cylinder 38 is forced out of that cylinder through the body fluid flow path 10 into the collection means 11. Thus, as long as the piston 40 is reciprocated and the inlet valve means 26 and outlet valve means 28 are controlled in the manner described above, fluid will be continually pumped from the interior of the patient's body 14 into the collection means 11.

The second reciprocating pumping means 36 operates in the same manner as the first reciprocating pumping means 34. Since the discharge or outlet 22 of the second flow path 18 joins the first flow path 10 upstream of the first reciprocating pumping means 34, the second reciprocating pumping means 36 discharges fluid when the first reciprocating pumping means is drawing in fluid from the body of the patient 14. In other words, the first reciprocating pumping means 34 and the second reciprocating pumping means 36 are operated "180 degrees out of phase". Thus, the body fluid and additive fluid are mixed together during the suction stroke of the first reciprocating pumping means 34. The motor means 48 insures that the correct "timing" or phase relationship between the two reciprocating pumping means 34 and 36 are maintained in the proper synchronous relationship.

It should be understood that if fluid is being drawn by the first reciprocating pumping means 34 from the body of the patient 14 at the same time that the second reciprocating pumping means 36 is discharging additive fluid into the first or body fluid flow path 10, that the two fluids are mixed at the confluence 24 of the two flow paths. Thus, by maintaining the two pumping means 34 and 36 in the correct time and phase relationship, additive fluids (such as an anticoagulant) can be added to a body fluid (such as lymph drawn from the thoracic duct) in a preselected proportion so as to produce a predetermined mixture of additive fluid and body fluid. This mixture is then discharged out of the end 13 of the first flow path 10 that is joined to the collection chamber 11.

The proper mixture or concentration of the two fluids is determined by the amount of additive fluid discharged by the second reciprocating pumping means 36 in relation to the amount of body fluid drawn by the first reciprocating pumping means 34. Either the stroke of the pistons 40 and 44 or the size of the cylinders 35 and 38 may be changed to control the concentration of the mixture of body fluid and additive fluid. In particular, by forming the pistons 40 and 44 and cylinders 35 and 38 from readily available disposible syringes of different sizes, the flow rate and concentration of the mixture of additive and body fluid may be easily regulated. All that one needs to do to change the reciprocating pumping means from one size to another is to change the size of the syringe used.

The motor means 48 will now be described. As previously explained, the function of the motor means 48 is to stroke the two pistons 40 and 44 in each of the two reciprocating pumping means 34 and 36 and operate the inlet valve means 26 and 30 and the outlet valve means 28 and 32 in each of the two flow paths 10 and 18. Preferably, the motor means 48 is carried by the frame 9 in such a manner that the major components 8 can be strapped to the patient (by a strapping means 200A, 200B) without unnecessarily immobilizing the patient.

Figure 3A:
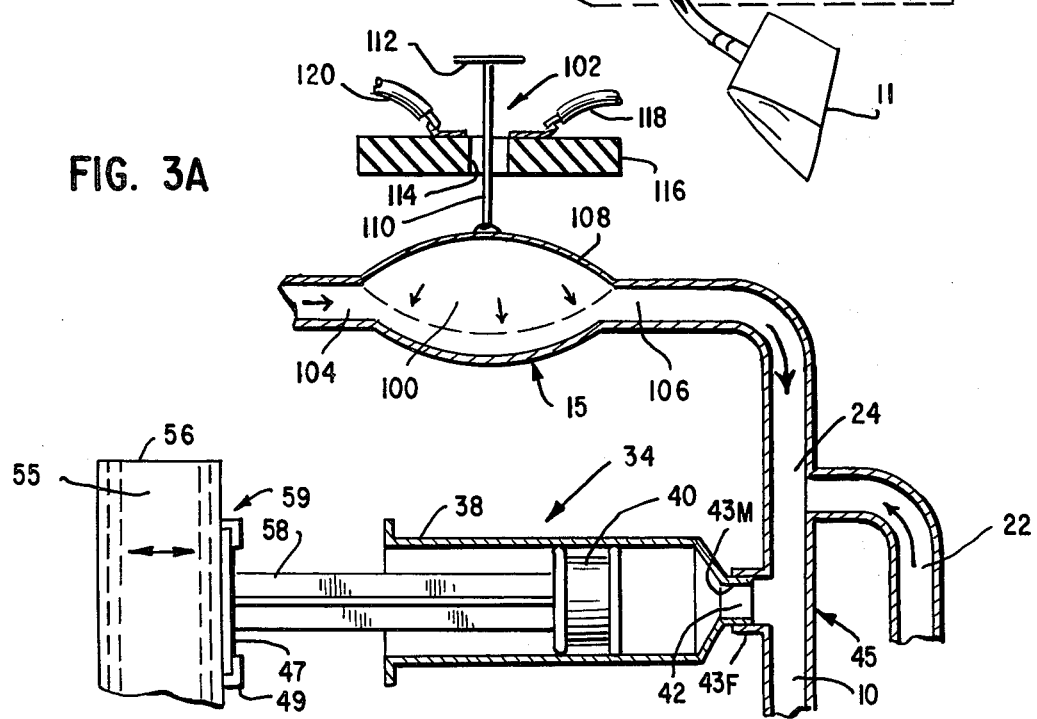
FIG. 3A is an enlarged view of a portion of the apparatus shown in FIGS. 1 and 2 illustrating one embodiment of the fluid pressure sensor means.

As shown in FIG. 1 the two pistons 40 and 44 are reciprocated by a linkage that is a variation of a "Scotch Yoke." Specifically, a crank 50 is rotated at a uniform angular velocity by a shaft 52 joined to an electric motor (not shown). Batteries can be used to power the electric motor. When the frame 9 is joined to the patient's body, the batteries can be carried in a belt worn by the patient. Such an arrangement allows the patient some freedom and does not unduly restrict him to a fixed position (such as a bed). The free end 54 of the crank fits within a yoke 55. One end 56 of the yoke 55 is joined to a connecting rod 58 attached to the first piston 40. The opposite end 60 of the yoke 55 is joined to a connecting rod 62 attached to the second piston 44. The yoke 55 is constrained by guides (not shown) to move in a direction perpendicular to its length. The connecting rods 58 and 62 are joined to the yoke 55 by a connection means 57 and 59. As shown in FIG. 3A the connection means 59 is a tongue and groove arrangement. The tongue 47 is attached to the rod 58 and the complementary groove or slot 49 is attached to the yoke 55. This allows the connecting rod 58 to by quickly joined to the yoke 55 without any special tools.

The frictional fit between the tongue 47 and groove 49 holds the connecting rod 58 secured to the yoke 55. As previously mentioned, the reciprocating pumping means 34 may be fabricated from a disposible syringe. The discharge port or opening 42 of the syringe barrel or cylinder 38 is frictionally joined to the first flow path 10 by simply slipping the female opening 43F of the "T-connection" 45 over the male opening 43M of the syringe barrel or cylinder 38. This technique allows the flow capacity of the two reciprocating pumping means 34 and 36 to be quickly and easily changed. Furthermore, it allows components to be easily changed should they fail or become inoperative. Alternatively, the flow capacity of the two reciprocating pumping means 34 and 36 may be adjusted by varying the speed of the motor rotating the shaft 52. A reduction gear and a variable speed transmission are two other devices which may be used to adjust the speed of the shaft 52 and thus the flow capacity of the two reciprocating pumping means 34 and 36.

Figure 4:
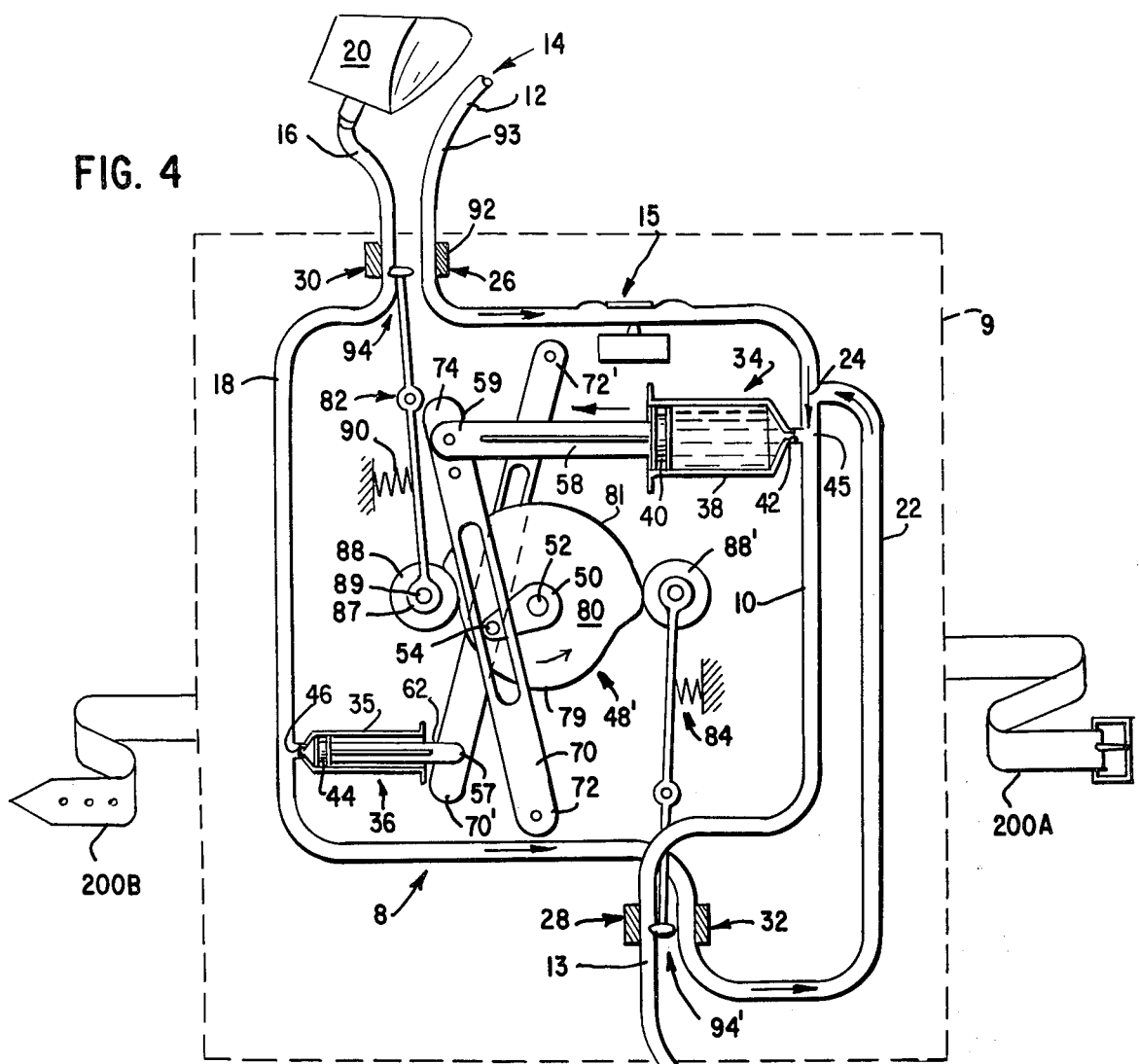
FIG. 4 is an enlarged, partial, schematic diagram of a second embodiment of the motor means used to drive the apparatus shown in FIGS. 1 and 2.

Another mechanism or linkage that can be used to stroke the two pistons 40 and 44 in the two reciprocating pumping means 36 and 38 is shown in FIG. 4. Just as in the mechanism previously described, a crank 50 is rotated at a uniform angular velocity by a shaft 52 joined to a motor (not shown). Please note that the crank 50 in FIG. 4 is rotated counterclockwise. The free end of the crank 54 fits within a slotted link 70. One end 72 of the slotted link 70 is pivotally joined to a fixed point on the frame 9. The opposite end 74 of the slotted link 70 is joined to the connecting rod 58 joined to the first piston 40. A similar linkage 70' is provided to operate the second reciprocating pumping means 36.

Those skilled in the art of mechanical linkages and mechanisms will recognize this as being a "quick return linkage." Specifically, such a linkage produces reciprocating motion such that the stroke in one direction is faster than the stroke in the opposite direction. As shown in FIG. 4, as the crank 50 rotates counterclockwise from the nine o'clock to the three o'clock position, the speed of the free end 74 of the slotted link 70 is greater than the speed of the free end when the slotted link is rotated counterclockwise from the three o'clock to the nine o'clock position. Since the crank 50 is rotated at a uniform speed, the free end 74 of the slotted link 70 must of necessity move at a slower speed when the free end 54 of the crank 50 is at its farthest distance from the fixed end 72 of the slotted link 70 relative to the speed at which the free end of the slotted link moves when the free end of the crank is closest to the fixed end of the slotted link. One advantage of a quick return linkage is that the linkage insures that fluid is drawn slowly into the first cylinder 38 while fluid is discharged from the first cylinder at a relatively higher flow rate. Drawing in fluid from the patient's body 14 slowly tends to minimize the pressure transient imposed on the duct in the patient's body from which the fluid is taken.

As shown in FIG. 4, a second quick return linkage 70' is used to operate the second reciprocating pumping means 36. There a separate crank (not shown) operates the second linkage 70'. A single crank may be used to position both linkages 70 and 70'.

As explained previously, the sequencing of the inlet valve means 26 and 30 and the outlet valve means 28 and 32 must be synchronized with the operation of the pistons 40 and 44 in the first and the second reciprocating pumping means 34 and 36 if additive fluid is to be mixed with the body fluid before the mixture is discharged to the collection flask 11 by the first reciprocating pumping means 34. In FIGS. 1, 3, and 4 a cam and follower mechanism is used to synchronize the operation of the valve means in relationship to the pumps. Specifically, the shaft 52 drives a cam 80 having two lobes 79 and 81 which in turn position a pair of spring loaded followers 82 and 84. Since each of the followers are of identical construction only one, the first follower, 82 will be described in detail. It should be noted, however, that two cams may be employed, one for each follower. The two cams may be arranged so that the actuation of the inlet and outlet valve means "overlap" (i.e., a certain amount of "dwell" can be introduced) during which time both inlet and outlet valve means in any one of the flow paths 10 and 18 are open or both are shut. For example, by having both the inlet and the outlet valve means 26, and 28 shut in the body fluid flow path 10 before the outlet valve means 28 is opened, there is no point in time that, in the event the motor driving the shaft 52 should fail, an unobstructed fluid path is formed between the duct in the patients body 14 and the collection means 11. It is conceivable that a "siphon effect" could be produced if both valves are open and the two pumping means are stopped whereby the fluid in the collection chamber 11 or in the reservoir 20 of additive fluid would "back-flow" into the patients body 14. Those skilled in the art should consider this possibility in making the apparatus that is the subject of this invention.

The first follower 82 (see FIG. 1) is formed from a link 85 pivoted at a point 86 intermediate its ends. One end 87 of the link 85 is rotatably joined to a roller 88 by a pin 89. A spring or biasing means 90 holds the roller 88 against the cam 80. Thus, as the cam 80 is rotated the roller 88 is forced inwardly and outwardly relative to the center of the cam by virtue of the spring 90 pushing the link 85 against the two lobes 79 and 81 of the cam.

In the embodiments illustrated in the figures, the valving function at the inlets 12 and 19 and the outlets 13 and 22 of the two flow paths 10 and 18 is produced by squeezing or pinching together the walls of a flexible tube when flow must be cut off and relaxing or releasing the pinched tube when flow is to be restored. Since each of the valve means 26, 28, 30 and 32 functions in the same manner only one 26 will be described in detail. At this point, it should be mentioned that one or more of the valve means may be a check valve (i.e., spring loaded, lift check, etc.). Check valves suitable for this service are known to those skilled in the art. Illustrations of typical check valves are found in laboratory and hospital equipment catalogs. The suction and discharge forces that are produced by the first and second pumping means 34 and 36 are used to actuate the associated check valves. One advantage of using check valves is that one or both follower mechanisms 82 and 84 may be eliminated. However, a check valve may produce a greater pressure drop than a similar length of plastic tubing. Consequently, the amount of fluid pumped may be reduced when check valves are employed. One advantage of employing a check valve as the valve means 92 at the inlet to the body fluid flow path 10 is that a check valve will automatically isolate the duct (from which the apparatus is drawing fluid in the patient's body 14) from the first and second reciprocating pumping means 34 and 36 in the event a high pressure condition is developed downstream the check valve. This would occur whether or not the motor means 48 is in operation or the pressure sensor means 75 (to be described in detail at a later point in this discussion) operates to shut off the first and second pumping means 34 and 36. The preferred embodiments are illustrated in the drawings and those embodiments do not employ check valves.

Figure 2:
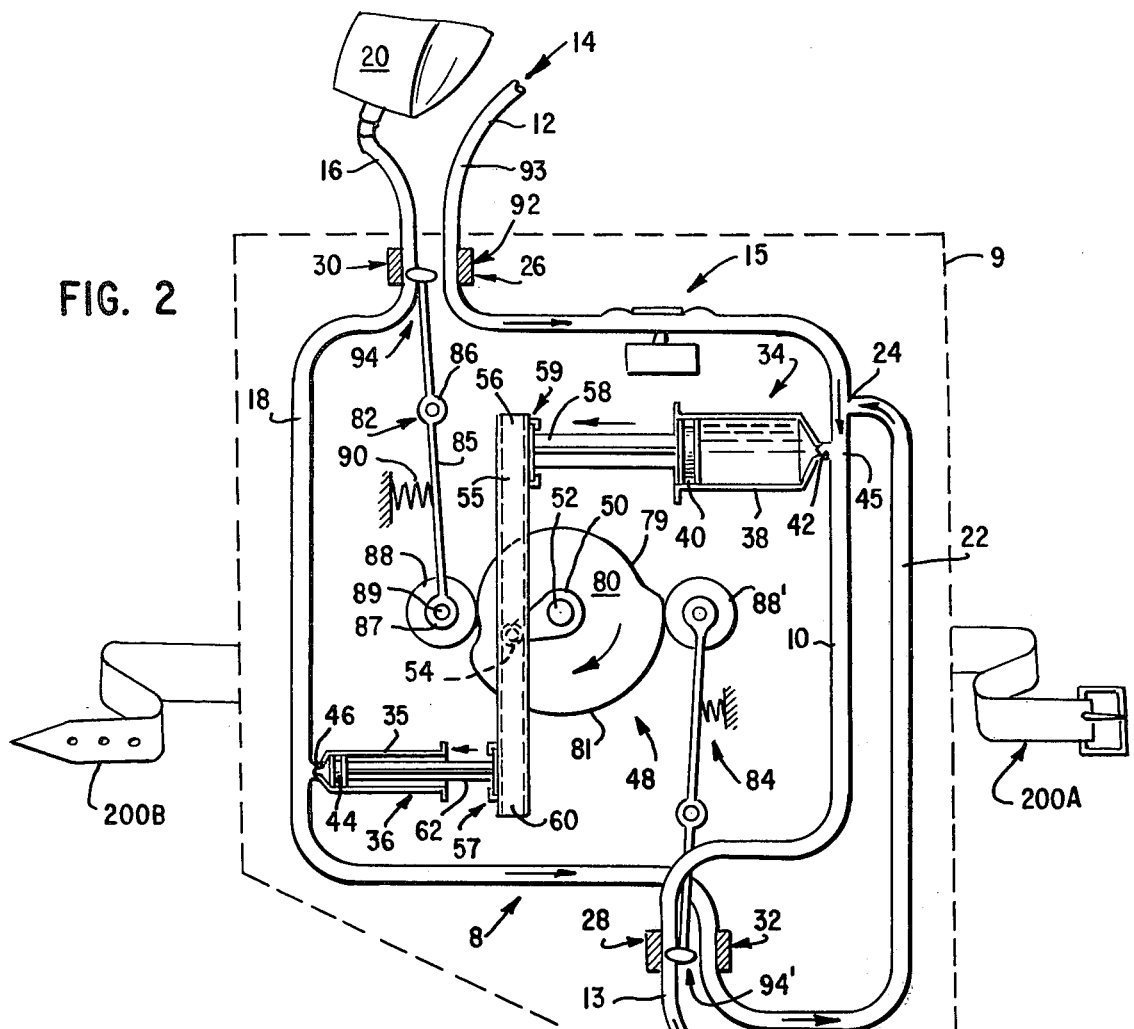
FIG. 2 is the same schematic diagram shown in FIG. 1 illustrating the major components of the present invention in a second position.

Referring to FIG. 1 the inlet valve means 26 at the inlet end 12 of the first or body fluid flow path 10 includes a stop or abutment 92 fixed to the frame 9, a length of flexible tubing 93 and a pinching means 94. The pinching means 94 pushes the walls of the flexible tube 93 against the stop 92 to cut off flow. When flow is to be restored the pinching means 94 moves sufficiently far from the stop 92 to allow the walls of the flexible tube 93 to expand thereby restoring flow. As shown in FIGS. 1 and 2, the pinching means 94 is a protruberance at the free end of the pivoted link 85 forming part of the first follower 82. Thus, as the cam 80 operates the follower 82, the protuberance or pinching means 94 is pushed towards and away from the walls of the tube 93 in such a manner as to sequentially cut off and restore flow.

It will be recalled that the first reciprocating pumping means 34 operates 180 degrees out of synchronization with the second reciprocating pumping means 36. As a consequence, the inlet valve means 26 to the first or body fluid flow path 10 is shut when the inlet valve means 30 to the second flow path 18 is opened (See FIG. 1). Similarly, the outlet valve means 28 for the first or body fluid flow path 10 is open when the outlet valve means 32 on the second flow path 18 is shut. This relationship is reversed when the first reciprocating pumping means 32 and the second reciprocating pumping means 36 change directions (see FIG. 2). Because of this relationship the same pinching means 94 can be used to cut off and restore flow for both inlet valve means 26 and 30. The same is true for the outlet valve means 28 and 32, that is, the same pinching means 94' can operate both valves.

Referring to FIGS. 1 and 2 and to the cam 80 and the two follower mechanisms 82 and 84 illustrated there, and remembering that for any one flow path 10 or 18, the inlet valve means 26 or 30 is always positioned opposite to the corresponding outlet valve means 28 or 32, it should be apparent that the rollers 88 and 88' are positioned relative to the cam lobes 79 and 81 in such a manner that one of the rollers rests on the outer lobe 81 whenever the other roller is on the inner lobe 79.

It should be appreciated from the foregoing discussion that any combination of the various linkages described can be used to produce the same effect. For example, FIGS. 1 and 2 illustrate the use of a cam and two follower mechanisms 82 and 84 to position the inlet 26 and 30 and outlet 28 and 32 valve means, and a modified version of a Scotch Yoke to operate the first and second reciprocating pumping means 34 and 36. On the other hand, FIG. 4 illustrates the use of a cam and two follower mechanisms 82 and 84 to position the inlet 26 and 30 and the outlet 28 and 32 valve means, and a variation of a quick return linkage to position the first 34 and second 36 reciprocating pumping means. Other variations and combinations may be used.

The last component to be described is the fluid pressure sensor means. The fluid pressure sensor means 15 is positioned in the body fluid flow path 10 downstream the inlet valve means 26 and upstream the first reciprocating pumping means 34. FIG. 3A is an enlarged detailed view of the fluid pressure sensor means 15 shown in FIGS. 1, 2, and 4. The function of the fluid pressure sensor means 15 is two-fold: (1) It reduces the pressure surges induced in the upstream end 12 of the body fluid flow path 10 and in the duct in the body of the patient 14 to which the first reciprocating pumping means 34 is attached; and (2) It shuts off the motor means 48 in the event that an abnormal pressure condition is created or detected in the upstream end 12 of the body fluid flow path.

The fluid pressure sensor means 15 has two major components: a variable volume chamber 100; and a switch means 102. The variable volume chamber 100 has an inlet 104 and an outlet 106. One wall 108 of the chamber 100 is formed from a material having a high coefficient of flexibility. In other words, this wall 108 will expand to a greater degree than the walls forming the inlet 104 or the outlet 106 of the chamber 100 or the walls of the tubing forming the body fluid flow path 10. In addition, this wall 108 preferably should have a higher coefficient of flexibility than that of the duct or passageway in the patient's body 14 to which the inlet 12 of the body fluid flow path 10 is connected. This latter characteristic insures that variable volume chamber 100 expands and contracts to a greater degree than the duct or passageway in the patient's body 14. The concern is that surges induced by the first reciprocating pumping means 38 may be transmitted to the relatively thin and fragile walls of the duct in the patient's body 14 to which the apparatus is attached. If the pressure imposed upon the walls of the duct in the body is sufficiently high, those walls may be ruptured. Conversely, if a high suction or negative pressure is produced on the walls of the duct, those walls may implode or collapse. If the wall 108 of the variable volume chamber 100 responds to pressure forces before the thin, fragile walls of the duct are flexed or pressurized, the duct is in effect protected from these pressure surges.

The second component of the fluid pressure sensor means 15 is the switch means 102. The switch means 102 is joined to the flexible wall 108 of the variable volume chamber 100 by a connecting rod 110. As shown in FIG. 3A, if a negative pressure were created at the inlet 12 to the body fluid flow path 10, the flexible wall 108 would collapse or would be drawn inwardly as shown by the dotted line and the downwardly directed arrows. If this condition is allowed to continue unabated, the walls of the duct in the patient's body 14 could collapse. The switch means 102 is used to interrupt power going to the motor driving the shaft 52 which is used to operate the two reciprocating pumping means 34 and 36 and the valve means 26, 28, 30, and 32. As illustrated in FIG. 3A the switch means 102 includes: a connecting rod 110 joined at one end to the flexible wall 108 of the variable volume chamber 100. The opposite end of the connecting rod 110 carries a bridge wire 112. The connecting rod 110 is free to move reciprocably through an opening 114 in a terminal board 116 attached to the frame 9. Two wires 118 and 120 are joined to the terminal board 116. When the bridge wire 112 connects together these two wires 118 and 120, an electrical circuit (not shown) is completed that shuts-off power to the motor means 48.

Figure 3B:
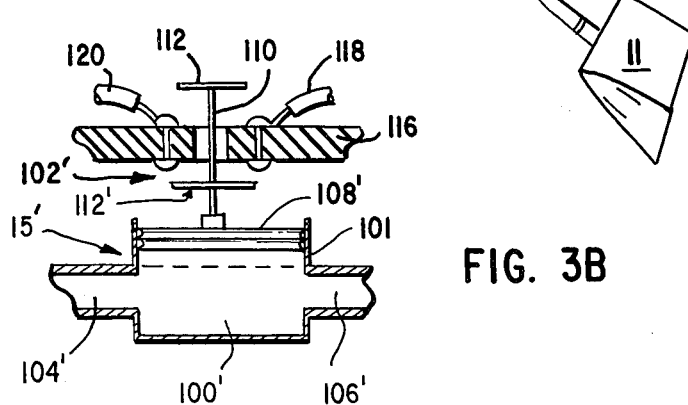
FIG. 3B is a second embodiment of the fluid pressure sensor means.

Another variation to this circuit is shown in FIG. 3B. The fluid pressure sensor means 15' shown in FIG. 3B employs a cylinder 101 opened at one end to form the variable volume chamber 100'. A piston 108' closes off the open end of the cylinder 101. Thus, as pressure increases or decreases in the upstream end 12 of the body fluid flow path 10, the piston 108' is driven inwardly or outwardly relative to the cylinder 101. Here, the switch means 102' has a second bridge wire 112' attached to the lower end of the connecting rod 110. The second bridge wire 112' completes the electrical path between the two wires 120 and 118 when the variable volume chamber 100' is driven outwardly. This could occur, for example, when the pressure in the upstream end 12 of body fluid flow path 10 is increasing or driven beyond a predetermined acceptable value. One cause for this could be an obstruction in any one of the lines forming the body fluid flow path 10 downstream of the first reciprocating pumping means 34. Effectively, the fluid would be forced to back flow into the upstream end 12 and back into the patient's body 14. Thus, the fluid pressure means 15' acts to shut off the motor means in the event of abnormally high pressure or an abnormally low pressure in the upstream end 12 of the body fluid flow path 10.

Other variations of the switch means 102 may be used. For example, the connecting rod may be joined to a wiper arm to which one 118 or 120 of the two wires 118 is directly connected. The wiper arm is driven reciprocally across a fixed conductor or contact bar joined directly to the other wire 120 or 118. In this circuit, current flows between the two wires 118 and 120 so long as the wiper arm lies between two ends of the contact bar. If the pressure in the variable volume chamber 100 becomes too high, the wiper arm is driven off one end of the contact bar. This interrupts the current flow to the motor means 48. Similarly, if the pressure in the variable volume chamber 100 becomes too low, the wiper arm is driven off the other end of the contact bar and the circuit between wires 118 and 120 is interrupted; again the motor means 48 is shut off. Other variations in the switch means 102 and the variable volume chamber 100 should be apparent to those skilled in the art from the foregoing description.

The overall operation of the invention will now be described. FIG. 1. illustrates the various components, linkages and valves at the end of the discharge stroke of the first reciprocating pumping means 34 and the end of the suction stroke of the second reciprocating pumping means 36. Consistent with these conditions the inlet valve means 26 in the body fluid flow path 10 is shut and the outlet valve means 28 for the body fluid flow path is open. Similarly, the inlet valve means 30 for the second flow path 18 is opened and the outlet valve means 32 for the second flow path 18 is shut. As the motor (not shown) drives the shaft 52 clockwise, the crank 50 is also driven clockwise. Consequently, the yoke 55, driven by the free end 54 of the crank 50, is driven from the right to the left end of the frame 9. This drives the piston 40 in the first reciprocating pumping means 34 outwardly and the piston 44 in the second reciprocating pumping means 36 inwardly.

Simultaneous with the movement of the yoke 55 the double lobed cam 80 is rotated clockwise. As the cam 80 is driven clockwise, the first follower 84 is repositioned from the inner lobe 79 to the outer lobe 81. Conversely, the second follower 82 is repositioned from the outer lobe 81 to the inner lobe 79. Repositioning the two followers 82 and 84 repositions the inlet valve means 26 and 30 and the outlet valve means 28 and 32 in the two flow paths 10 and 18. Repositioning the valves as indicated above is consistent with the first reciprocating pumping means 34 drawing fluid from the patient's body 14 and the second reciprocating pumping means 36 forcing additive fluid into the body fluid flow path 10 at the confluence 34 of the two flow paths 10 and 18.

FIG. 2 illustrates the position of the various components at the end of the suction stroke of the first reciprocating pumping means 34 at the end of the discharge stroke of the second reciprocating pumping means 36. Again, consistent with the discussion above, the inlet valve means 26 to the body fluid flow path 10 is open and the inlet valve means 30 to the second flow path 18 is shut. Also, the outlet valve means 28 for the body fluid flow path 10 is shut and the outlet valve means 32 of the second fluid flow path 18 is open. The flow of fluid is indicated by the arrows. Continued clockwise rotation of the shaft 52 will drive the yoke 55 from the left to the right which forces fluid out of the first cylinder 38 into the collection means 11 and draws fluid into the second cylinder 35. Since the mixture of body fluid and additive fluid is discharged at a positive pressure, the mixture can flow through components such as filters, membranes, etc. located downstream the outlet end 13 of the body fluid flow path 10.

Continued clockwise rotation of the cam 80 will result in the two followers 82 and 84 repositioning such that the valves will shift position to that shown in FIG. 1. This cycle will be repeated as long as the motor means 48 continues to operate.

If at any time the pressure in the inlet 12 to the first reciprocating pumping means 34 becomes abnormal, the fluid pressure sensor means 15, 15' will be actuated to shut off the motor means 48 which shuts down the entire apparatus. A suitable warning device (not shown) can be provided to alert personnel of the problem so that they may take remedial action. Once the problem is corrected the motor means 48 can be reactivated and pumping cycle continued.

Thus, it is apparent that there has been provided in accordance with the present invention, a unique and novel apparatus suitable for use in drawing fluid from a patient's body which at the same time mixes with that fluid an additive in a prescribed proportion so long as the apparatus is in operation. Inherent design features are not only provided to insure that fluid is properly drawn from the body but also features are provided to shut off the apparatus in the event that an abnormal pressure condition is created or detected.

While the invention has been described in conjunction with certain specific embodiments, it is evident that many alternatives, modifications, and variations will be apparent to those skilled in the art in light of the foregoing detailed description. Accordingly, it is intended to cover all such alternatives, modifications, and variations as set forth within the spirit and broad scope of the appended claims.

What is as claimed is as follows:

1. Apparatus suitable for withdrawing a body fluid from a duct in a patient comprising:
   (a) a frame;
   (b) first reciprocating pumping means, mounted on said frame, for pumping body fluid, said first pumping means including a body fluid reservoir and a first piston plugging said fluid reservoir at one end, said fluid reservoir having an opening at the opposite end defining the inlet and outlet of said first pumping means, said first piston being free to move reciprocatingly within said fluid reservoir between an "in" and an "out" position, thereby defining the suction and discharge strokes of said first pumping means;

(c) a body fluid passageway associated with said frame and having an inlet end and an outlet end, said body fluid passageway being in communication with said opening in said body fluid reservoir at a location intermediate the inlet and outlet ends of said body fluid passageway;

(d) second reciprocating pumping means, mounted on said frame, for pumping liquid, said second pumping means including a liquid reservoir and a second piston plugging said liquid reservoir at one end, said liquid reservoir having an opening at the opposite end defining the inlet and outlet of said second pumping means, said second piston being free to move reciprocatingly within said liquid reservoir between an "in" and an "out" position;

(e) a liquid passageway associated with said frame and having an intake end and a discharge end, said liquid passageway being in communication with said opening in said liquid reservoir at a location intermediate said intake end and discharge end;

(f) first and second valving means, situated respectively at said body fluid passageway inlet end and outlet end and means operatively connecting said first and second valve means with said first pumping means, for controlling fluid flow therethrough, said first and second valving means each having open and shut positions;

(g) third and fourth valving means, situated respectively, at said liquid passageway intake end and discharge end and means operatively connecting said first and second valve means with said second pumping means, for controlling liquid flow therethrough, said third and fourth valving means each having open and shut positions; and (h) motor means, mounted on said frame, for operating said first and second pumping means to induce flow through said body fluid passageway and through said liquid passageway, the discharge end of said liquid passageway communicating with said body fluid passageway at a location upstream of the inlet to said first pumping means whereby liquid flowing out of said liquid passageway is commingled with the body fluid in said body fluid passageway as an aliquot of the body fluid is drawn into said body fluid reservoir by the reciprocating action of said first pumping means.

2. The apparatus defined in claim 1, wherein one of said first and second valving means is a check valve.

3. The apparatus defined in claim 1, wherein one of said third and fourth valving means is a check valve.

4. The apparatus defined in claim 1, wherein said motor means actuates at least one of said said first and second valving means.

5. The apparatus defined in claim 1, wherein said motor means actuates at least one of said third and fourth valving means.

6. The apparatus defined in claim 1, wherein said first and said second valving means are opened and shut by means of a linkage pivotably mounted on said frame and actuated by said motor means.

7. The apparatus defined in claim 1, wherein said motor means includes:

(a) prime mover means, carried by said frame;

(b) a crank rotatable about a fixed axis relative to said frame and operably associated with said prime mover means; and (c) linkage means, carried by said frame and driven by said crank, for actuating said first piston reciprocatingly in a cycle between its in position and its out position, the speed of said first piston relative to said frame when moving from said out position to said in position being greater than the relative speed of said first piston when moving from said in position to said out position whereby fluid is drawn into said body fluid reservoir at a slower rate than fluid is discharged from said body fluid reservoir.

8. The apparatus defined in claim 7, wherein said linkage means actuates said first valving means whereby said first valving means is opened and shut in synchronism with the operation of said first pumping means.

9. The apparatus defined in claim 1, further including: variable volume chamber means, carried by said frame and in fluid communication with the suction side of said first pumping means, for moderating the pressure surges induced in said body fluid passageway by the operation of said first pumping means and said second pumping means, the fluid volume of said chamber means expanding in response to increasing pressure in said suction side and contracting in response to decreasing pressure in said suction side, the expansion and contraction of said chamber means dissipating pressure exerted on said suction side.

10. The apparatus defined in claim 9, further including: a switch actuated by said chamber means, the expansion and contraction of said chamber means operating said switch between an "on" position and an "off" position, the position of said switch being representative of the pressure condition within said duct.

11. The apparatus defined in claim 1, further including: fluid pressure sensor means, carried by said frame, for generating a control signal having a characteristic which varies in direct response to the pressure condition in said body fluid passageway upstream from said first pumping means; and means for sensing said variations in said control signal characteristic and for de-energizing said motor means in response to said characteristic achieving a preselected value.

12. The apparatus defined in claim 11, wherein said fluid pressure sensor means includes:

(a) a length of elastomeric tubing having a wall portion that is free to (1) expand to increase the fluid volume of said tubing in response to increasing fluid pressure within said tubing and (2) contract to decrease the fluid volume of said tubing in response to increasing fluid pressure within said tubing; and (b) switch means, carried by said length of elastomeric tubing, for de-energizing said motor means in response to said wall portion contracting to a first pre-defined volume representative of said tubing being pressurized to a first pre-selected pressure or de-energizing said motor means in response to said wall portion expanding to a second pre-defined volume representative of said tubing being pressurized to a second pre-selected pressure, whereby said first pumping means and said second pumping means are cycled on and off to maintain the pressure upstream said body fluid passageway between said first and second preselected pressure.

13. The apparatus defined in claim 12, wherein said tubing is formed from silicone rubber having a stiffness substantially less than the stiffness of said body fluid passageway and said duct.

14. The apparatus defined in claim 1, further including: strapping means for removably joining said frame to an external portion of the human body.

15. The apparatus defined in claim 1, wherein said second pumping means has a lower flow capacity than said first pumping means.

16. The apparatus defined in claim 1, wherein at least one of said first and said second valving means includes: a flexible tube; and pinching means for pinching said tube to shut-off flow through said tube and for releasing said tube to restore flow through said tube thereby shutting and opening said one valving means, said pinching means being actuated by said motor means.

17. The apparatus defined in claim 16, wherein said motor means includes:
(a) a prime mover connected to a shaft for producing shaft rotation;
(b) a cam mounted on said shaft and a follower, said cam and follower coacting to control the operation and sequencing of said pinching means to open and shut said one valving means.

18. The apparatus defined in claim 17, wherein said one valving means is said first valving means, said cam operating said follower to actuate said pinching means to shut-off flow through the inlet during the discharge stroke of said first pumping means, said cam operating said follower to actuate said pinching means to restore flow through said inlet end during the discharge stroke of said first pumping means.

19. The apparatus defined in claim 16, wherein said pinching means includes: a link pivoted at a point intermediate its ends to said frame with one end of said link having a protrusion abutting said flexible tube, said flexible tube being juxtaposed between said protrusion and fixed portion of said frame, the opposite end of said link being reciprocated by said motor means between a first position and a second position, said link in said first position cam pressing a portion of the walls of said tube between said protrusion and said frame to shut-off flow through said tube, said link in said second position releasing said tube to restore flow through said tube.

20. The apparatus defined in claim 19, wherein said motor means includes: a cam rotated about a fixed axis on said frame with the opposite end of said link operatively connected to said cam to reciprocate said one end between said first position and said second position.

21. The apparatus defined in claim 20, further including a means for biasing said link to one of said first or second positions, said opposite end of said link including a roller riding against said cam, whereby said link is moved to the other of said first or second positions in response to said cam cooperating with said roller to oppose said biasing means at least during a portion of the rotational cycle of said cam.

22. The apparatus defined in claim 1, wherein said motor means includes a Scotch Yoke reciprocatingly carried by said frame and joined to said first piston and said second piston, whereby said first piston and said second piston are reciprocated within said body fluid reservoir and said liquid reservoir respectfully.

23. The apparatus defined in claim 1, wherein said motor means reciprocates said first piston outwardly away from the inlet to said body fluid reservoir while recriprocating said second piston inwardly towards the inlet to said liquid reservoir whereby fluid is drawn into said first pumping means while liquid is discharged from said second pumping means.

24. The apparatus defined in claim 1, further including: connection means for removably connecting said first piston in said first reciprocating pumping means to said motor means.

25. The apparatus defined in claim 1, wherein said body fluid reservoir is removably joined to said body fluid passageway.

* * * * *